United States Patent [19]
Takahashi et al.

[11] Patent Number: 5,908,956
[45] Date of Patent: Jun. 1, 1999

[54] METHOD FOR PRODUCING TRIMETHYLHYDROQUINONE DIESTER

[75] Inventors: Ikuo Takahashi, Kobe; Masahiro Chikamori, Hyogo, both of Japan

[73] Assignee: Daicel Chemical Industries, Ltd., Osaka, Japan

[21] Appl. No.: 08/991,897

[22] Filed: Dec. 17, 1997

[30] Foreign Application Priority Data

Dec. 27, 1996 [JP] Japan .................................. 8-350456

[51] Int. Cl.$^6$ .................................. C07C 67/48
[52] U.S. Cl. ...................... 560/79; 560/231; 568/341; 568/763
[58] Field of Search .................. 568/763, 341; 560/79, 231

[56] References Cited

FOREIGN PATENT DOCUMENTS

| | | |
|---|---|---|
| 808815 | 5/1997 | European Pat. Off. . |
| 2149159 | 4/1972 | Germany . |
| 47-007632 | 4/1972 | Japan . |
| 47-7632 | 4/1972 | Japan . |

OTHER PUBLICATIONS

Corma et al, Journal of Catalysis, vol. 120, pp. 78–87, 1989.

*Primary Examiner*—Gary Geist
*Assistant Examiner*—Sreeni Padmanabhan
*Attorney, Agent, or Firm*—Birch, Stewart, Kolasch & Birch, LLP

[57] ABSTRACT

This method provides trimethylhydroquinone diester by using a recyclable catalyst which shows high activity and operability in the reaction, while reducing the risk of corrosion of the reactor. The method for the production of 2,5,6-trimethylhydroquinone diester comprises reacting 2,6,6-trimethylcyclohexe-2-en-1,4-dione with an acylating agent in the presence of a solid catalyst. The acylating agent includes a $C_{2-4}$ carboxylic acid anhydride (e.g. acetic anhydride) and a $C_{2-4}$ carboxylic acid halide (e.g. acetyl chloride). The solid catalyst includes a solid acid catalyst (e.g. strongly or super-strongly acidic ion exchange resin, compound oxide, zeolite, heteropoly acid).

8 Claims, No Drawings

METHOD FOR PRODUCING TRIMETHYLHYDROQUINONE DIESTER

FIELD OF THE INVENTION

The present invention relates to a method for producing trimethylhydroquinone diester by allowing 2,6,6-trimethylcyclohexe-2-en-1,4-dione with an acylating agent in the presence of a solid catalyst.

BACKGROUND OF THE INVENTION

Trimethylhydroquinone diester and its hydrolysed product, trimethylhydroquinone, are advantageously used as an intermediate of pharmaceuticals. Specifically, they are used as a raw material for vitamin E, an anti-oxidant for resins, higher fatty acids, higher alcohols and oils, and a polymerisation inhibitor for polymerisable monomers, thus considered important in the industrial point of view.

Japanese Patent Application Laid-open No. 7632/1972 (JP-A-47-7632) teaches a method for producing trimethylhydroquinone diester by reacting 2,6,6-trimethylcyclohexe-2-en-1,4-dione (ketoisophorone, KIP) with an acylating agent in the presence of a protonic acid catalyst or a Lewis acid catalyst.

In this method, however, the protonic acid or the Lewis acid used as a catalyst has to be neutralised and separated after the reaction, which renders the process complicated. Besides, the yield of the produced trimethylhydroquinone diester decreases owing to hydrolysis which occurs during the neutralisation step. The method further requires a discarding step, because the catalyst, neutralised after the reaction, has to be thrown away after every reaction. Thus, it is impossible to recycle the catalyst effectively. The Lewis acid catalysts inclusive of $BF_3OEt_2$ are expensive, and thus should not be disposed of for industrial advantages. As for reaction equipment, the reactor has to be made of a corrosion-resistant material, such as a glass-lining reactor and other specially made reactors, which are inevitably expensive.

SUMMARY OF THE INVENTION

It is therefore an object of the present invention to provide a method for producing trimethylhydroquinone diester at a high selectivity and yield, in which a high reactivity is exhibited between 2,6,6-trimethylcyclohexe-2-en-1,4-dione (ketoisophorone, KIP) and an acylating agent.

It is another object of the present invention to provide a method for producing trimethylhydroquinone diester which requires no post-reaction treatments such as neutralisation or removal of a catalyst, thus the method shows a high reaction operability.

It is a further object of the present invention to provide a method for producing trimethylhydroquinone diester, wherein a catalyst shows less of a decrease in its activity, can be used repeatedly, and is less corrosive to a reactor.

The inventors of the present invention have intensively researched to accomplish the above objects, and found that when trimethylhydroquinone diester is produced by reacting 2,6,6-trimethylcyclohexe-2-en-1,4-dione with an acylating agent in the presence of a solid catalyst, (i) the process is rewarded with an excellent reactivity; (ii) the catalyst does not need to be neutralised or removed after the reaction; and (iii) the catalyst, which shows less loss of its activity, can be used repeatedly, while being less corrosive to a reactor. The present invention is based on the above findings.

In the method of the present invention, trimethylhydroquinone diester as shown in the following formula (1) is produced by reacting 2,6,6-trimethylcyclohexe-2-en-1,4-dione with an acylating agent in the presence of a solid catalyst,

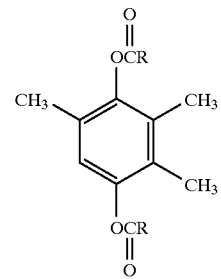

wherein R represents an alkyl group, a cycloalkyl group, an aryl group, or a heterocyclic group. As the solid catalyst, use can be made of a solid acid catalyst and so on.

DETAILED DESCRIPTION OF THE INVENTION

As the solid catalyst for the present invention, use can be made of a variety of solid compounds which act as a catalyst in the reaction of 2,6,6-trimethylcyclohexe-2-en-1,4-dione with the acylating agent. In particular, the solid catalysts include solid acid catalysts such as strongly or super-strongly acidic solid catalysts. Preferable solid acid catalysts are, for example, strongly acidic ion exchange resins (e.g. porous or non-porous ion exchange resins having a sulfonic acid group), super-strongly acidic ion exchange resins (e.g. porous or non-porous ion exchange resins having a super-strong acid group such as $-CF_2CF_2SO_3H$), sulfates (e.g. $CaSO_4$, $Fe_2(SO_4)_3$, $CuSO_4$, $NiSO_4$, $AlSO_4$, $MnSO_4$, $BaSO_4$, $CoSO_4$, $ZnSO_4$, $(NH_4)_2SO_4$), metal oxides (e.g. $SiO_2$, $Al_2O_3$, $TiO_2$, $Fe_2O_3$, $ZrO_2$, $SnO_2$), compound oxides (e.g. $SiO_2-Al_2O_3$, $SiO_2-TiO_2$, $TiO_2-ZrO_2$, $SiO_2-ZrO_2$), zeolites (e.g. Y-, X-, or A-type zeolite having an acidic OH group, ZSM5, moldenite, VPI5, $AlPO_4$-5, $AlPO_4$-11), kaolins, and heteropoly acids (e.g. heteropoly acids having an element such as P, Mo, V, W, and Si). Superstrong acids have a Hammett's acidity function $H_0$ of less than −11.93.

Among the solid acid catalysts, a specific example of the strongly acidic ion exchange resin is a styrene-divinylbenzenesulfonic acid-series ion exchange resin, "Amberlyst 15" (manufactured by Organo, Ltd.), and specific examples of the superstrongly acidic ion exchange resin include a fluorinated sulfonic acid-series resin, "Nafion NR50" (Aldrich, Inc.), "Nafion H" (Dupont, Inc.), etc.

The solid acid catalyst may be a solid acid catalyst which supports or holds a protonic acid (e.g. the above-mentioned superstrong acids and other protonic acids; strong acids) or a Lewis acid on a support (or a carrier) or a porous support (or carrier). As the acids to be supported (acid catalysts), there may be mentioned $SbF_5$, $TaF_5$, $BF_3$, $AlCl_3$, $AlBr_3$, $SbF_5$—HF, $SbF_5$—$FSO_3H$, $SbF_5$—$CF_3SO_3H$, $SO_4^{2-}$, and tungstic acid.

The support may be either porous or non-porous. Examples of the support are metal oxides (e.g. $SiO_2$, $Al_2O_3$, $TiO_2$, $Fe_2O_3$, $ZrO_2$, $SnO_2$), compound oxides (e.g. $SiO_2-Al_2O_3$, $SiO_2-TiO_2$, $TiO_2-ZrO_2$, $SiO_2-ZrO_2$), zeolites, graphites, Pt-graphites, ion exchange resins, metal sulfates, metal chlorides, metals (e.g. Pt, Au), alloys (e.g. Pt—Au, Ni—Mo, Al—Mg), polymers, salts (e.g. $SbF_3$, $AlF_3$), bauxites, activated carbons, charcoals and the like. The porous support is not specifically restricted in its surface area (e.g. 10 to 5,000 m²/g), pore volume, and average pore diameter. The amount of the acid catalyst to be supported is, for instance, about 0.1 to 50% by weight, preferably about 1 to 25% by weight.

To be specific, the catalysts supported on the carrier include $SbF_5/SiO_2$, $SbF_5/Al_2O_3$, $SbF_5/TiO_2$, $SbF_5/Fe_2O_3$, $SbF_5/ZrO_2$, $SbF_5/SnO_2$, $SbF_5/SiO_2$—$Al_2O_3$, $SbF_5/SiO_2$—$TiO_2$, $SbF_5/TiO_2$—$ZrO_2$, $SbF_5/SiO_2$—$ZrO_2$, $AlCl_3/CuSO_4$, $SbF_5$—$HF/Al_2O_3$, $SbF_5$—$HF/SiO_2$—$Al_2O_3$, $SbF_5$—$HF/$activated carbon, $SbF_5$—$FSO_3H/Al_2O_3$, $SbF_5$—$FSO_3H/SiO_2$—$Al_2O_3$, $SbF_5$—$FSO_3H/$activated carbon, $SO_4^{2-}/ZrO_2$ (sulfated zirconia), $SO_4^{2-}/TiO_2$ (sulfated titania), $SO_4^{2-}/Fe_2O_3$, $SO_4^{2-}/TiO_2$—$ZrO_2$, $WO_3/ZrO_2$, $Pt/SO_4^{2-}/ZrO_2$, and others.

The amount of the solid acid catalyst is determined, in accordance with the reaction conditions, in the range of effective amounts. For example, the amount is about 0.1 to 1,000 parts by weight, preferably about 1 to 100 parts by weight (e.g. 5 to 100 parts by weight), and more preferably about 2 to 50 parts by weight (e.g. 5 to 25 parts by weight), relative to 100 parts by weight of the substrate (e.g. KIP).

The solid catalyst may be used as a slurry in the reaction system, or may be charged in a column in which reactants are able to flow.

As the acylating agent, use may be made of an acylating agent containing an aliphatic hydrocarbon group, an alicyclic hydrocarbon group, an aromatic hydrocarbon group or a heterocyclic group, each of which corresponds to R in the formula (1). Specific examples of the acylating agent include acid anhydrides, acyl halides, enol esters, and the like.

As the acid anhydrides, there may be mentioned carboxylic acid anhydrides including, for instance, straight (straight-chain) or branched (branched-chain) $C_{1-10}$ alkyl-carboxylic acids (e.g. $C_{1-8}$ alkyl-carboxylic acids such as acetic acid, propionic acid, butyric acid, isobutyric acid, and valeric acid, particularly $C_{1-6}$ alkyl-carboxylic acids), alicyclic carboxylic acids (e.g. $C_{3-10}$ cycloalkyl-carboxylic acids such as cyclohexanecarboxylic acid), aromatic carboxylic acids (e.g. $C_{6-12}$ aryl-carboxylic acids such as benzoic acid and toluic acid), halogen-containing carboxylic acids (e.g. chloroacetic acid, trichloroacetic acid, trifluoroacetic acid), heterocyclic carboxylic acids (e.g. furancarboxylic acid, thiophenecarboxylic acid, nicotinic acid, pyridinecarboxylic acid), and other anhydrides. $C_{1-4}$ alkyl-carboxylic acid anhydrides (e.g. $C_{2-4}$ carboxylic acid anhydrides such as acetic anhydride and propionic anhydride) are particularly preferred among these.

As the acyl halides, there may be exemplified acyl halides which correspond to the above-mentioned acid anhydrides, including $C_{1-10}$ alkyl-carboxylic acid halides (e.g. $C_{1-8}$ alkyl-carboxylic acid halide such as acetyl chloride, propionyl chloride, and butyryl chloride), alicyclic carboxylic acid halides (e.g. cyclohexanecarboxylic acid halide), aromatic carboxylic acid halides (e.g. benzoic acid halide), heterocyclic carboxylic acid halides (e.g. furancarboxylic acid halide), and the like. Among them, $C_{1-4}$ alkyl-carboxylic acid halides (e.g. $C_{2-4}$ carboxylic acid halides such as acetyl chloride and propionyl chloride) are desirable.

As the enol esters, there may be mentioned isopropenyl acetate, isopropenyl propionate, isopropenyl isobutyrate, isopropenyl butyrate, cyclohexenyl benzoate, and so on.

These acylating agents can be used in a molar quantity of at least about twice (e.g. 2 to 10 times), preferably about 3 to 10 times, relative to the substrate KIP. An excess amount of the acylating agent may be used as the solvent.

The reaction of the 2,6,6-trimethylcyclohexe-2-en-1,4-dione with the acylating agent provides the 2,5,6-trimethylhydroquinone diester of the formula (1) at a high conversion and selectivity.

In the formula (1), the group represented by R corresponds to the aforesaid acylating agent. Examples of the alkyl group include $C_{1-10}$ alkyl groups (e.g. methyl, ethyl, butyl, isobutyl, t-butyl, pentyl, hexyl and other $C_{1-8}$ alkyl groups). Examples of the cycloalkyl group include $C_{3-10}$ cycloalkyl groups (e.g. cyclohexyl group). Examples of the aryl group include $C_{6-12}$ aryl groups (e.g. phenyl group, p-methylphenyl group and other substituted phenyl groups). Examples of the heterocyclic group include aromatic or nonaromatic 5- or 6-membered heterocyclic groups which contain at least one hetero atom selected from a nitrogen, oxygen, or sulfur atom (e.g. furyl group, thienyl group, nicotinyl group, pyridyl group).

The trimethylhydroquinone diester shown by the formula (1) corresponds to the acylating agent used for its production. By way of illustration, use of acetic anhydride or acetyl chloride provides trimethylhydroquinone diacetate; use of propionic anhydride provides trimethylhydroquinone dipropionic acid ester; and use of benzoic anhydride gives trimethylhydroquinone dibenzoic acid ester.

The reaction of the present invention may be conducted in the presence of or the absence of a solvent. Inert solvents include straight or branched, saturated or unsaturated hydrocarbons (e.g. aliphatic hydrocarbons including hexane, heptane, and octane; alicyclic hydrocarbons including cyclohexane; unsaturated aliphatic or alicyclic hydrocarbons including octene and cyclohexene; aromatic hydrocarbons including benzene, toluene, and xylene), organic acids (e.g. acetic acid, propionic acid, butyric acid, lactic acid, trichloroacetic acid, trifluoroacetic acid), esters (e.g. methyl acetate, ethyl acetate, butyl acetate), halogen-containing solvents (e.g. methylene chloride, chloroform, carbon tetrachloride, 1,2-dichloroethane, chlorobenzene, dichlorobenzene), ethers (e.g. diethyl ether, diisopropyl ether, dibutyl ether, tetrahydrofuran, dioxane, ethylene glycol dimethyl ether, diethylene glycol dimethyl ether), ketones (e.g. acetone, methyl ethyl ketone, methyl isobutyl ketone, diisobutyl ketone), nonprotonic polar solvents (e.g. amides including dimethylformamide and dimethylacetoamide; amines including N-methylpyrrolidone; sulfoxides including dimethylsulfoxide; nitriles including acetonitrile and benzonitrile; nitroes including nitromethane, nitroethane, and nitrobenzene), etc. These solvents can be used alone or as a mixture of two or more species.

The amount of the solvent is not particularly limited, and is about 0 to 50% by weight, preferably about 0 to 30% by weight, based on the amount of the reaction system.

In the reaction system of the present invention, the concentration of the substrate, 2,6,6-trimethylcyclohexe-2-en-1,4-dione, is not strictly limited. For instance, the concentration may be about 5 to 40% by weight, preferably about 10 to 35% by weight.

The reaction temperature can be selected from the range of about 0 to 150° C., preferably about 10 to 120° C. (e.g. 10 to 100° C.), practically, it being about 50 to 110° C. If the reaction temperature is too high, the object compound may be coloured and be produced only in a lower yield. On the other hand, if the temperature is too low, the reaction may proceed at an extremely slow rate.

After the reaction is completed, the reaction mixture is separated and purified by a conventional process (e.g. filtration, concentration, distillation, crystallisation, extraction, or a combination of these processes), without any operation for the neutralisation or separation of the catalyst, to give the 2,5,6-trimethylhydroquinone diester.

The solid catalyst separated from the reaction mixture by filtration or the like can be recycled into the reaction system, after being washed where necessary. Thus, the catalyst can be used over and over again.

The 2,5,6-trimethylhydroquinone which corresponds to the compound of the formula (1) may be provided by way of hydrolysis of the reaction mixture containing trimethylhydroquinone diester.

The method of the present invention serves to raise the reactivity in the reaction of 2,6,6-trimethylcyclohexe-2-en-1,4-dione and the acylating agent, thereby contributing to an efficient production of trimethylhydroquinone diester. After the reaction, this method requires no neutralisation or removal of the catalyst, while inhibiting the decrease in the catalytic activity, so that the catalyst can be reutilised. Further, with the catalyst being less corrosive to the reactor, trimethylhydroquinone diester is produced with great advantages both industrially and economically.

The following examples are intended to illustrate the present invention in more detail but should by no means limit the scope of the invention.

EXAMPLES

Example 1

Charged into a three-neck flask were 1 g of a strongly acidic ion exchange resin "Amberlyst 15" (manufactured by Organo, Ltd.) as the catalyst, 10 g (0.066 mole) of 2,6,6-trimethylcyclohexe-2-en-1,4-dione, and 20 g (0.196 mole) of acetic anhydride. The mixture was allowed to react for six hours at 60° C. After the completion of the reaction, a gas chromatographic analysis showed that 2,6,6-trimethylcyclohexe-2-en-1,4-dione, the raw material, was completely consumed (conversion: 100%), and that 2,5,6-trimethylhydroquinone diacetate was produced at a yield of 88%. The catalyst was separated from the reaction mixture by filtration. The filtrate was concentrated and then crystallised using a mixed solvent of ethyl acetate and hexane. This process provided 2,5,6-trimethylhydroquinone diacetate at a yield of 60%, whose melting point was between 109 and 110° C.

Example 2

The reaction process of Example 1 was followed, except for using 15 g (0.145 mole) of acetic anhydride and performing the reaction for five hours at 80° C. Gas chromatography after the reaction proved complete consumption of the raw-material 2,6,6-trimethylcyclohexe-2-en-1,4-dione and production of trimethylhydroquinone diacetate at a yield of 84%. After being filtered off from the catalyst, the filtrate was concentrated, and thereafter crystallised with the use of an ethyl acetate/hexane solvent. Trimethylhydroquinone diacetate was thus provided at a yield of 55%.

Example 3

The catalyst used in Example 1 was reutilised after being washed with methanol and dried. After the completion of a reaction conducted in the same manner as in Example 1, a gas chromatographic analysis showed complete consumption of the material 2,6,6-trimethylcyclohexe-2-en-1,4-dione, and production of trimethylhydroquinone diacetate at a yield of 86%.

Example 4

Charged into a 100-ml three-neck flask were 1 g of a super-strongly acidic ion exchange resin "Nafion NR50" (manufactured by Aldrich, Inc.) as the catalyst, 10 g (0.066 mole) of 2,6,6-trimethylcyclohexe-2-en-1,4-dione, and 20 g (0.196 mole) of acetic anhydride. The mixture was allowed to react for six hours at 100° C. After the completion of the reaction, a gas chromatographic analysis showed that 2,6,6-trimethylcyclohexe-2-en-1,4-dione, the raw material, was completely consumed, and that 2,5,6-trimethylhydroquinone diacetate was produced at a yield of 85%. The catalyst was separated from the reaction mixture by filtration. The filtrate was concentrated and then crystallised using a mixed solvent of ethyl acetate and hexane. This process provided 2,5,6-trimethylhydroquinone diacetate at a yield of 60%, whose melting point was between 109 and 110° C.

Example 5

Charged into a 100-ml three-neck flask were 1 g of a protonic Y-type zeolite (Si/Al=5) as the catalyst, 10 g (0.066 mole) of 2,6,6-trimethylcyclohexe-2-en-1,4-dione, and 20 g (0.196 mole) of acetic anhydride. The mixture was allowed to react for 16 hours at 100° C. After the completion of the reaction, a gas chromatographic analysis showed complete consumption of the 2,6,6-trimethylcyclohexe-2-en-1,4-dione, the raw material, and production of trimethylhydroquinone diacetate at a yield of 75%.

Example 6

Charged into a 100-ml three-neck flask were 1 g of sulfated zirconia as the catalyst, 10 g (0.066 mole) of 2,6,6-trimethylcyclohexe-2-en-1,4-dione, and 20 g (0.196 mole) of acetic anhydride. The mixture was allowed to react for 10 hours at 80° C. A gas chromatographic analysis after the reaction showed 74% consumption of the 2,6,6-trimethylcyclohexe-2-en-1,4-dione, the raw material, and 52% yield of trimethylhydroquinone diacetate.

Example 7

Except for using toluene as the solvent, the reaction was conducted in the same manner as in Example 1. A gas chromatographic analysis after the reaction provided 65% consumption of the raw-material 2,6,6-trimethylcyclohexe-2-en-1,4-dione, and 51% yield of trimethylhydroquinone diacetate.

Example 8

Except for using 27.3 g (0.196 mole) of propionic anhydride instead of acetic anhydride, the reaction was conducted as in Example 1. A gas chromatographic analysis after the reaction proved 100% consumption of the raw-material 2,6,6-trimethylcyclohexe-2-en-1,4-dione, and 82% yield of trimethylhydroquinone diacetate.

Example 9

After repeating the reaction of Example 1 and observing complete consumption of the 2,6,6-trimethylcyclohexe-2-en-1,4-dione, the reaction mixture was allowed, with an addition of water (30 g), to undergo a hydrolysis reaction at 100° C. for four hours. After the completion of the reaction, gas chromatography found no trimethylhydroquinone diacetate, but provided trimethylhydroquinone at 78%. The reaction mixture was filtered to remove the catalyst. The filtrate was then concentrated and crystallised using ethanol and water, whereby trimethylhydroquinone was obtained at a yield of 55%.

Comparative Example 1

Charged into a three-neck glass flask were 10 g (0.066 mole) of 2,6,6-trimethylcyclohexe-2-en-1,4-dione, 20 g (0.196 mole) of acetic anhydride, and 0.4 g (4 mmole) of sulfuric acid as a catalyst. The mixture was allowed to react at 50° C. for 14 hours. After the completion of the reaction, a gas chromatographic analysis showed complete consumption of the raw material, 2,6,6-trimethylcyclohexe-2-en-1,4-dione, and production of 2,5,6-trimethylhydroquinone diacetate at a yield of 90%. The reaction mixture was neutralised using a 2 N aqueous solution of sodium hydroxide. Dimethyl ether was added to the neutralised mixture, which was then filtered. The filtrate was concentrated under reduced pressure to give a crude product. The crude product was re-crystallised using hexane, and thereafter, subjected to filtration, washing and drying. Thus, 2,5,6-trimethylhydroquinone diacetate having a melting point of 101 to 108° C. was obtained at a yield of 46%.

What is claimed is:

1. A method for producing trimethylhydroquinone diester shown by the formula (1),

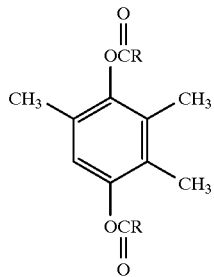

wherein R represents an alkyl group, a cycloalkyl group, an aryl group or a heterocyclic group, by allowing 2,6,6-trimethylcyclohex-2-ene-1,4-dione to react with an acylating agent in the presence of a solid catalyst selected from the group consisting of ion exchange resins having a sulfonic acid group and acidic solid catalysts having a Hammet's acidity function $H_0$ of less than −11.93.

2. A method as claimed in claim 1, wherein R is a $C_{1-3}$ alkyl group.

3. A method as claimed in claim 1, wherein R is a methyl group.

4. A method as claimed in claim 1, wherein said acylating agent a $C_{2-4}$ carboxylic acid anhydride or a $C_{2-4}$ carboxylic acid halide.

5. A method as claimed in claim 1, wherein said acylating agent is acetic anhydride or acetyl chloride.

6. The method of claim 1, wherein the acylating agent is an acid anhydride selected from the group consisting of straight or branched-chain $C_{1-10}$ alkyl-carboxylic acids, $C_{3-10}$ alicyclic carboxylic acids, $C_{6-12}$ aryl-carboxylic acids, halogen-containing carboxylic acids, and heterocyclic carboxylic acids.

7. The method of claim 1, wherein the acylating agent is an acyl halide selected from the group consisting of $C_{1-10}$ alkyl-carboxylic acid halides, alicyclic carboxylic acid halides, aromatic carboxylic acid halides, and heterocyclic carboxylic acid halides.

8. The method of claim 1, wherein the acylating agent is an enol ester selected from the group consisting of isopropenyl acetate, isopropenyl propionate, isopropenyl isobutyrate, isopropenyl butyrate, and cyclohexenyl benzoate.

* * * * *